United States Patent
Boate et al.

(10) Patent No.: US 7,310,734 B2
(45) Date of Patent: Dec. 18, 2007

(54) METHOD AND SYSTEM FOR SECURING A COMPUTER NETWORK AND PERSONAL IDENTIFICATION DEVICE USED THEREIN FOR CONTROLLING ACCESS TO NETWORK COMPONENTS

(75) Inventors: Alan Boate, Ottawa (CA); Brian Reed, Stittsville (CA)

(73) Assignee: 3M Innovative Properties Company, St. Paul, MN (US)

( * ) Notice: Subject to any disclaimer, the term of this patent is extended or adjusted under 35 U.S.C. 154(b) by 759 days.

(21) Appl. No.: 09/775,205

(22) Filed: Feb. 1, 2001

(65) Prior Publication Data

US 2002/0104006 A1    Aug. 1, 2002

(51) Int. Cl.
*H04K 3/00* (2006.01)
*G06F 12/16* (2006.01)
*G06F 11/30* (2006.01)

(52) U.S. Cl. ............... 713/186; 713/193; 713/176; 380/270; 726/5

(58) Field of Classification Search ............... 713/186, 713/193, 176; 380/270; 726/5
See application file for complete search history.

(56) References Cited

U.S. PATENT DOCUMENTS

| | | | |
|---|---|---|---|
| 4,582,985 A | | 4/1986 | Lofberg |
| 4,816,653 A | | 3/1989 | Anderl et al. |
| 4,816,654 A | | 3/1989 | Anderl et al. |
| 5,131,038 A | * | 7/1992 | Puhl et al. ............ 340/5.61 |
| 5,229,764 A | | 7/1993 | Matchett et al. |
| 5,568,552 A | * | 10/1996 | Davis ..................... 705/59 |
| 5,579,393 A | | 11/1996 | Conner et al. |
| 5,613,012 A | | 3/1997 | Hoffman et al. |
| 5,623,552 A | | 4/1997 | Lane |
| 5,787,186 A | | 7/1998 | Schroeder |
| 5,823,948 A | | 10/1998 | Ross, Jr. et al. |

(Continued)

FOREIGN PATENT DOCUMENTS

EP    0973 125    5/1995

(Continued)

OTHER PUBLICATIONS

*Identification and Authentication when Users have Multiple Accounts*, W.R. Shockely, 1993 ACM 0-89791-635-2, pp. 185 to 191.

(Continued)

*Primary Examiner*—Nasser Moazzami
*Assistant Examiner*—Eleni A Shiferaw
(74) *Attorney, Agent, or Firm*—Melissa E. Buss (57) ABSTRACT

An improved computer network security system and a personal identifier device used for controlling network with real time authentication of both a person's identity and presence at a computer workstation is provided. A new user is registered to a portable personal digital identifier device and, within the portable personal digital identifier device, an input biometric of the user is received and a master template is derived therefrom and securely maintained in storage. A private key and public key encryption system is utilized to authenticate a user registered to the portable personal digital identifier device. The personal digital identifier device verifies the origin of a digitally signed challenge message from the network security manager component. A digitally and biometrically signed challenge response message is produced and transmitted by the personal digital identifier device in response to the verified challenge message.

21 Claims, 7 Drawing Sheets

U.S. PATENT DOCUMENTS

| | | | |
|---|---|---|---|
| 5,877,675 A * | 3/1999 | Rebstock et al. | 340/286.07 |
| 5,960,085 A | 9/1999 | de la Huerga | |
| 6,016,476 A | 1/2000 | Maes et al. | |
| 6,018,801 A | 1/2000 | Palage et al. | |
| 6,028,950 A * | 2/2000 | Merjanian | 382/126 |
| 6,037,879 A | 3/2000 | Tuttle | |
| 6,039,251 A | 3/2000 | Holowko et al. | |
| 6,040,783 A | 3/2000 | Houvener et al. | |
| 6,045,039 A | 4/2000 | Stinson et al. | |
| 6,088,450 A * | 7/2000 | Davis et al. | 713/182 |
| 6,092,202 A | 7/2000 | Veil et al. | |
| 6,122,625 A | 9/2000 | Rosen | |
| 6,131,090 A | 10/2000 | Basso, Jr. et al. | |
| RE36,946 E | 11/2000 | Diffie et al. | |
| 6,148,342 A | 11/2000 | Ho | |
| 6,195,564 B1 * | 2/2001 | Rydbeck et al. | 455/557 |
| 6,255,944 B1 * | 7/2001 | Addy | 340/539.3 |
| 6,353,889 B1 | 3/2002 | Hollingshead | |
| 6,400,996 B1 * | 6/2002 | Hoffberg et al. | 700/83 |
| 6,408,330 B1 * | 6/2002 | DeLaHuerga | 709/217 |
| 6,418,424 B1 * | 7/2002 | Hoffberg et al. | 706/21 |
| 6,480,096 B1 * | 11/2002 | Gutman et al. | 340/5.31 |
| 6,484,260 B1 * | 11/2002 | Scott et al. | 713/186 |
| 6,577,734 B1 * | 6/2003 | Etzel et al. | 380/277 |
| 6,594,762 B1 * | 7/2003 | Doub et al. | 726/35 |
| 6,607,136 B1 * | 8/2003 | Atsmon et al. | 235/492 |
| 6,754,504 B1 * | 6/2004 | Reed | 455/517 |
| 6,763,315 B2 * | 7/2004 | Xydis | 702/127 |
| 6,819,219 B1 * | 11/2004 | Bolle et al. | 340/5.52 |
| 2001/0020254 A1 * | 9/2001 | Blumenau et al. | 709/229 |
| 2001/0036821 A1 * | 11/2001 | Gainsboro et al. | 455/410 |
| 2002/0039907 A1 * | 4/2002 | McKenna et al. | 455/517 |
| 2002/0073042 A1 * | 6/2002 | Maritzen et al. | 705/64 |
| 2002/0191765 A1 * | 12/2002 | Labaton | 379/201.01 |
| 2003/0005300 A1 * | 1/2003 | Noble et al. | 713/172 |

FOREIGN PATENT DOCUMENTS

| | | |
|---|---|---|
| EP | 1 045 346 A2 | 10/2000 |
| GB | 2 312 040 | 10/1997 |
| GB | 2 348 309 | 9/2000 |
| WO | WO 98/13791 | 4/1998 |
| WO | WO 99/13415 | 3/1999 |
| WO | WO 99/22330 | 5/1999 |
| WO | WO 99/56429 | 11/1999 |
| WO | WO 00/26823 | 5/2000 |
| WO | WO 00/42678 | 7/2000 |

OTHER PUBLICATIONS

*A survey of routing techniques for mobile communications networks*, S. Ramanathan and Martha Steenstrup, Mobile Networks and Applications 1 (1996) pp. 89-104.

*Trust and Traceability in Electronic Commerce*, Dennis D. Steinauer, Shukri A. Wakid, Stanley Raspberry, StandardView vol. 5, No. 3, Sep. 1997, pp. 118 to 124.

*Authentication via Keystroke Dynamics*, Fabian Monrose, Aviel Rubin, 1997 ACM 0-89791-912-2/97/04, pp. 48 to 56.

*Experiences with network-based used agents for mobile applications*, Thomas F. La Porta, Ramachandran Ramjee, Thomas Woo and Krishnan K. Sabnani, Mobile Networks and Applications 3 (1998) pp. 123 to 141.

*A public-key based secure Mobile IP\**, John Zao, Stephen Kent, Joshua Gahm, Gregory Toxel, Matthew Condell, Pam Helinek, Nina Yuan and Isidro Castineyra, Wireless Networks 5 (1999) pp. 373 to 390.

*Biometric Identification*, Anil Jain, Lin Hong and Sharath Pankanti, 2000 ACM 0002-0782/00/0200.

\* cited by examiner

METHOD AND SYSTEM FOR SECURING A COMPUTER NETWORK AND PERSONAL IDENTIFICATION DEVICE USED THEREIN FOR CONTROLLING ACCESS TO NETWORK COMPONENTS

FIELD OF THE INVENTION

This invention relates to means for securing computer networks and, in particular, to a digital personal identifier device incorporated into a computer network and used for securely authenticating an individual holder thereof and for controlling the scope of that individual's access to components of the computer network.

BACKGROUND OF THE INVENTION

Protecting electronic information is a growing worldwide concern. Whether the information consists of intellectual property, vital operational data or personal information the costs of unintentional exposure are increasing due to global competition, public awareness of data privacy issues and new legislation. These problems are compounded by pervasive network technologies, which enable access to data from virtually any location and a multitude of access devices. For example, regulatory requirements affecting some industries, such as the health care industry in the U.S. (where rules are being adopted to ensure that health care facilities take all reasonable measures to ensure the security and privacy of individually identifiable health information), create an increasing need to be able to authenticate each prospective user of a computer network before such person is permitted access to the network or to data therein which may be considered sensitive or confidential.

Each component of a network, and each pathway between such components, can become the subject of an attack (i.e. to permit data access by an unauthorized entity). Moreover, the ability to access confidential data over a network does not necessarily require that a person log into the network because an unauthorized observer within viewing distance of a network computer screen may be able to access confidential data simply by viewing the screen when it displays such data. Thus, the usual approaches to achieving data access protection which target user authentication to provide such protection are able to address only the problem of unauthorized network users and not that of unauthorized observers who never attempt to access the network through use.

Cryptography is frequently employed within networked systems as a security measure and uses private and public keys. The terms "private key" and "public key" are well known in the art and are used for asymmetric cryptography in which one key is used for encryption and the other for decryption and one of these keys, namely the private key, is kept by the user and never revealed or transferred. Asymmetric cryptography is considered to provide a higher level of security than symmetric cryptography for which a shared key is used for both encryption and decryption (the sharing aspect introducing an element of insecurity). Using asymmetric cryptography to send a message to another party, the public key of that party is located using a public key infrastructure (PKI) and used to encrypt the message and then only the person with the corresponding private key (i.e. being the other party for whom the message is created) is able to decrypt the message.

The term digital signature is also well known in the art and refers to a message digest encrypted using a private key, a message digest being a condensed form of a document or transaction to be signed which cannot be used to recreate the document or transaction itself, and which is extremely sensitive to small changes in the document. The digital signature is verified by decrypting it with the corresponding public key to recover the message digest and then comparing this message digest with one computed by a verifier from the document which was purported to be signed. This technique can be used as part of an authentication process in which a party proves they have a specific private key by their ability to encrypt and return a message digest. In this case, the specific contents of the message are not crucial and the message digest may be discarded after authentication is complete. More commonly, the encrypted message digest will be used to prove that the holder of a specific key was involved in a transaction involving the message, usually to indicate that they gave their assent to the message, just as a physical signature is used to indicate the participation of its owner in a document. In this case, the encrypted form of the digest must be retained at a secure site. Both forms of digital signature are used as part of the present invention.

User identification systems frequently use passwords, smart cards, biometrics, and/or PKI (Public Key Infrastructure) security measures and while they may focus on securing portions of the authentication process the known systems leave open other avenues of attack. For example, software only systems rely on something the user knows such as a user name and password which can be fairly readily stolen, seen or otherwise acquired and then used by unauthorized persons. Security means based on tokens (i.e. something the user has), such as smart cards, are similarly vulnerable since the token can be lost or stolen and, therefore, does not guarantee that the authorized user is actually present.

Security means based on biometric identifiers (i.e. something the user is) can be equally vulnerable to unauthorized intervention. For example, any use of a central server to validate a presented biometric introduces a security weakness because of the need to transport the critical biometric data over either (or both) of the communications channels to be engaged for such remote validation (i.e. between the biometric transducer which captures the presented biometric and the local computer, and between the local computer and the validating central server containing the verification data with which the presented biometric is compared). Therefore, the manner in which a biometric identifier is handled and processed is critical if it is to function effectively as a security measure.

There is a need not only to identify the potential points of failure by which a computer network might become subject to unauthorized infiltration but also to develop means for addressing and reducing such areas of vulnerability in a comprehensive manner. Security breaches may occur in various forms, including the following: replay (referring to a situation where a former response element is captured and used to interject a false response), snooping (referring to unauthorized observation), spoofing (referring to the situation where an imposter inserts itself and manager both reception and transmission such that it appears to be a genuine element of the network) and/or tailgating (referring to a situation of unauthorized access acquired by joining with an authorized access sequence when it is abandoned by the authorized user).

It is important to avoid vulnerability caused by time gaps and/or one-way verification checks during the identification/validation processes. The applicants herein recognize a need for verification check processes to take place in real time, and for reciprocal verification checks between the central verification authority and the local entity being verified, in order to protect against some types of security breaches.

There is also a need for means to automatically and effectively monitor and control, and to generate an audit trail for, persons having authority for differing levels of access to the network (e.g. full access and limited access).

SUMMARY OF THE INVENTION

In accordance with the invention there are provided an improved network security system and method, and a personal identifier device used for controlling network access, to provide real time authentication of both a person's identity and presence at a particular network access point. Contemporaneous application of biometric verification and cryptography is provided on-board the portable, personal digital identifier device to provide authenticated digital signatures which are used for establishing secure access to data stored on a network and for performing secure transactions over a network.

A security system in accordance with the invention controls access to a computer network at a network access point comprising a workstation e.g. personal computer (PC). A personal digital identifier device comprises: (a) a wireless communications component comprising a transceiver; (b) a biometric acquisition component containing a transducer and a software component for obtaining a user's input biometric and producing a digital representation thereof; (c) a processor configured for communicating with the transceiver and the biometric component and operable for: (i) evaluating whether a template derived from the digital representation corresponds to a master template derived from a user's biometric digital representation previously produced by the biometric component and generating a matching signal when such a correspondence is determined; (ii) generating a private key to be held by the personal digital identifier device and a public key corresponding thereto and outputting the generated public key for transmission by the transceiver; (iii) producing a digital signature using the private key; and, (iv) verifying that an encrypted received message is from a security manager component using a public key for a private key associated with the security manager component; and, (d) secure storage containing the master template of a user's biometric, the generated private key and the public key for the private key associated with the security manager component. The personal digital identifier device is configured for producing a digitally signed challenge response message, using the generated private key, following the generating of the matching signal in response to a challenge received from the security manager component and for transmitting the response message. The personal digital identifier device is further configured to prevent transmission of any of the master template of a user's biometric and the private key.

A base unit is associated with the workstation and is configured for initiating and maintaining wireless communications with the personal digital identifier device. The communications extend over an area defined by an envelope associated with the workstation, the shape and area of the envelope being configured to encompass those locations proximate to the workstation at which an observer may read and/or understand information displayed on a screen of the workstation.

A secure central server has access to network storage and utilizes the security manager component and the personal digital identifier device to authenticate the user. The network storage contains a public key corresponding to the private key generated by the personal digital identifier device.

Preferably the base unit regularly transmits a first signal to the personal digital identifier device and the personal digital identifier device automatically transmits a response signal in response thereto when the personal digital identifier device is within the envelope. The system preferably comprises a plurality of the personal digital identifier devices, a plurality of workstations and a plurality of base units wherein a base unit is associated with each the workstation and each base unit transmits a polling signal to each personal digital identifier device within the base unit's associated envelope following the base unit's receipt of the response signal from each personal digital identifier device.

Preferably, all data held in the secure storage of the personal digital identifier device is by itself non-identifiable of the user and the network storage includes data identifiable of the user which is displayed on a screen of the workstation when the user's personal identification device is located within the envelope.

Preferably, once the user has been authenticated for access to the network at the workstation, the user's access to applications through the network is determined by a policy manager component which directs the security manager component.

BRIEF DESCRIPTION OF THE DRAWINGS

Reference will now be made to the accompanying drawings which illustrate, by way of example, a preferred embodiment of the present invention (and in which like reference numerals refer throughout to like elements).

DETAILED DESCRIPTION OF THE ILLUSTRATED PREFERRED EMBODIMENT

Figure 1:
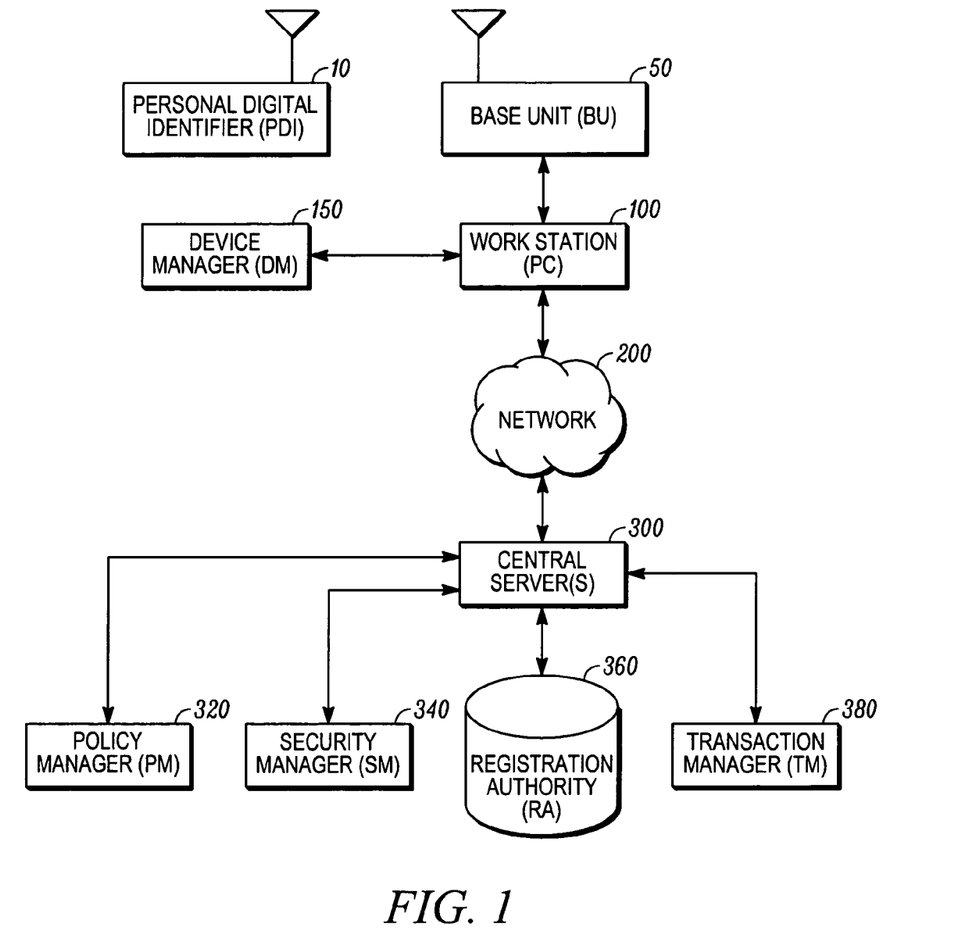
FIG. 1 is a general block diagram of the system of the present invention for securing a communications network by controlling access thereto.

A preferred security system in accordance with the invention is shown in FIG. 1 of the drawings. A plurality of workstations 100, being personal computers (PCs) in the preferred embodiment, communicate through a network 200 being any one of a global communications network, wide area network (WAN), metro area network (MAN) or local area network (LAN). At each such PC 100 which provides an access point to the network 200 there are a base unit (BU) device 50 connected to the PC's communications port (being the USB port in the illustrated embodiment) and a device manager (DM) 150 software component which relays messages such as those between the BU 50 and a secure central server 300. One or more personal digital identifier (PDIs) devices 10 communicate with the BU 50 when the PDI is within a predetermined detection envelope associated with the PC 100 and BU 50 connected thereto. The PDI 10 communicates with the BU 50 using wireless communications (IR being used for this embodiment but other optical or RF means being available for use in other possible alternative embodiments) and is issued to and carried or worn by those individuals who are permitted access to the network through the PC 100.

The BU 50 communicates with the PDI 10 using the same wireless communications means and automatically initiates communications with any such PDI 10 located within the detection envelope. This detection envelope is established so as to extend over the area in front of and to the side of the display screen of the PC 100 such that it includes any person/PDI pair who is close enough to see the screen and able to read or understand the contents displayed on the screen. By so configuring the communications envelope between the BU 50/PC 100 pair and the PDI 10 the security system detects all PDI's as and when the persons wearing them come into effective viewing range of a PC 100.

The PC 100 communicates through the network 200 with secure central server(s) 300 on which security manager (SM) 340, policy manager (PM) 320 and transaction manager (TM) 380 applications run. The transaction manager 380 manages all communications between the secure cental server(s) 300 and other devices on the network, including the device manager 150 and any relevant applications running on the PC 100 or on other network servers. The security manager 340 directs all actions involving cryptography and digital signatures. The policy manager 320 determines whether a user's access to applications or data on the network is to be limited and, if so, directs the security manager 340 to limit the user's access accordingly. A registration authority (RA) component 360, comprising a software component (viz. a registration application suite) and a secure database, is accessed through the central server 300.

Figure 2:
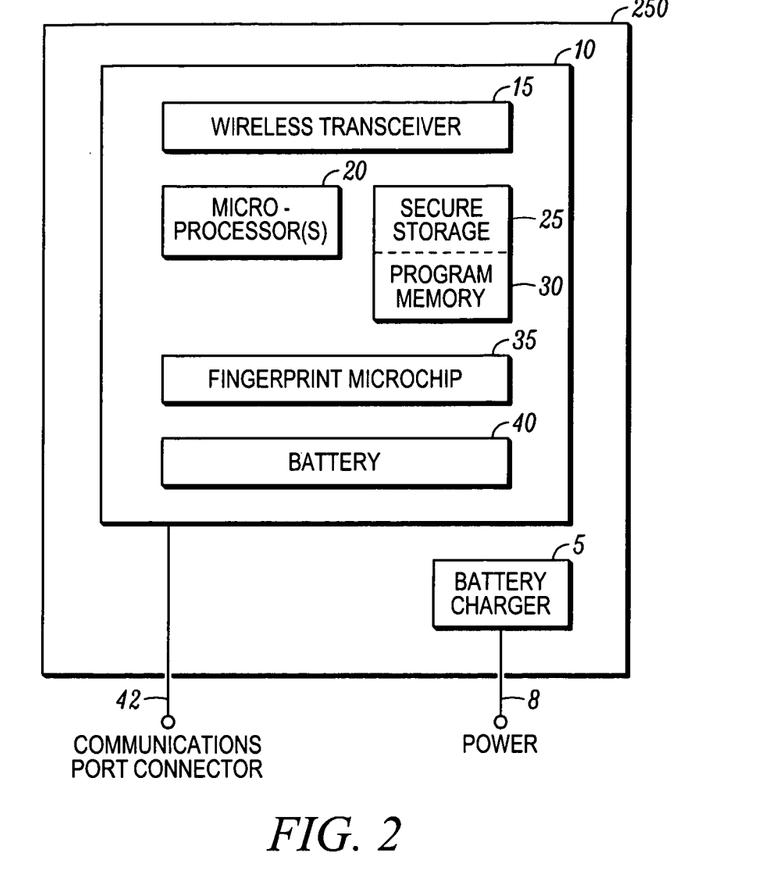
FIG. 2 is a schematic block diagram showing components of a personal digital identifier device (PDI) in accordance with the present invention, wherein the PDI is positioned on a recharging device holder (cradle) for network access from a secure single-user location.

Referring to FIG. 2, the PDI device 10 contains only a small amount of circuitry and is simple, lightweight and wearable. The PDI 10 includes a biometric acquisition component 35 which, in the illustrated embodiment, includes a fingerprint microchip transducer which takes an image of the user's finger using a solid state, non-optical sensor, to confirm the user's identity. Transducers for sensing other types of biometrics, such as voice characteristics, iris pattern and facial features and converting them into representative signals are other options which are available for use in a different embodiment where appropriate. Microprocessor(s) 20 are provided to process the user's biometric enrollment and verification, to create and verify digital signatures and to implement asymmetrical and/or symmetrical cryptography. Secure storage 25, as is well known in the art, is provided to securely store only cryptographic keys and the user's biometric template. No individually identifiable data (i.e. data which itself directly or indirectly identifies the user) is stored on the PDI 10 because this might then enable a very skilled unauthorized third party to acquire both the identity of the user and that user's biometric template in the event that such party were to be somehow able to penetrate the secure storage and gain access to the data stored therein. A wireless communications transceiver 15 permits short range wireless communications (using near infrared at 890 nm). A rechargeable battery 40 feeds a power management system to allow the PDI 10 to run continuously for an appropriate time period (e.g. 2 weeks or longer). Each PDI 10 has a globally unique identification (ID) number assigned to it and, therefore, each device is recognizable by its ID number. A battery charger 5 is also provided to recharge the battery 40 of the PDI 10 and a recharging device holder (cradle) 250 may be used to connect the PDI 10 directly to the PC 100 by means of a communications port connector 42 (e.g. USB connector) which connects to the PC's communications port, this direct connection (i.e. tethered mode in which a BU 50 is not needed or used for that PC 100) being useful to achieve a secure log-on to the network from a secure location where only a single user is expected to be present, for example a home office. The device holder is configured to co-operate with the housing of the PDI so that the PDI is securely held by the device holder when the PDI is positioned appropriately relative to the device holder.

Figure 3:
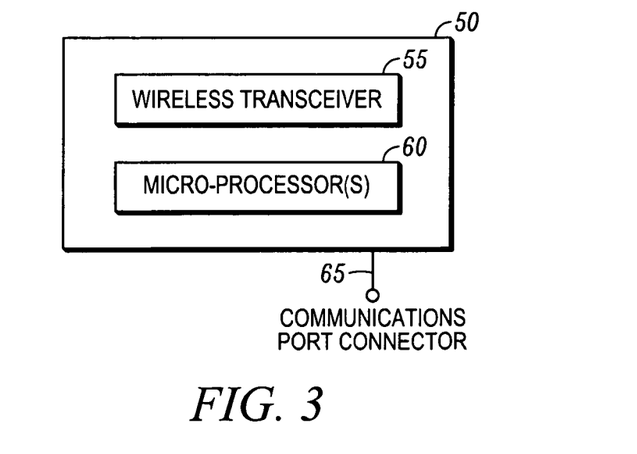
FIG. 3 is a block diagram showing components of a base unit (BU) of the security system of the present invention.

Referring to FIG. 3, the base unit (BU) device 50 also includes a wireless communications transceiver 55 permitting short range wireless communications (using near infrared at 890 nm). The transceiver 55 and positioning of the BU 50 are configured, as stated, to enable reception of any PDI 10 within a predetermined detection envelope surrounding the PC 100. Microprocessor(s) 60 manage communications between the PDI 10 (or PDIs if more than one PDI is in wireless communication range of the BU) and the BU 50 and between the BU 50 and the PC 100. A communications port connector 65 (e.g. USB connector) is provided to connect the BU 50 to the host PC 100.

Each PDI 10 and BU 50 includes a combination of hardware and software which controls the operation of the transceivers 10, 55, respectively, so that they operate with range and angle characteristics closely approximating the ability of the human eye to read the display screen of an associated PC 100 so that the presence of any person/PDI pair close enough to that host PC to read or understand data on its display screen is detected by the BU 50. The shape and size of the detection envelope are controllable and may be varied through a combination of hardware and software changes applied to the BU and PDI to suit local PC/workstation configurations or organization requirements. One skilled in the art is readily able to achieve such variations as desired for any given configuration. The communications software allows any and all PDIs 10, within such predetermined detection envelope, to be acquired by the base unit 50 and the base unit maintains communications which each such PDI, in the form of a conversation, for so long as they are within the detection envelope. The conversations comprise encrypted streams of data and are configured to permit detection of any other device attempting to join into the conversation. To simplify the continuation of this conversation when the user briefly turns away or otherwise obscures the optical path between the PDI 10 and the BU 50, it is possible to include a second transceiver on both the PDI and the BU which uses a non-directional communications mode such as short range radio-frequency (RF) waves. This mode will not be used to begin a conversation, but can keep it going for short periods of time.

Each PDI 10 also includes a cryptographic software component which manages the creation of one or more public/private key pairs within the PDI 10 and all subsequent processing on the PDI 10 involving encrypting and decrypting messages. The authenticity of the PDI 10 is confirmed through a communications protocol whereby an on-board (i.e. contained within the PDI) private key is used to digitally sign a challenge sent to the PDI by the security manager component (SM) 340 which runs on the central server 300 of the network. Importantly, the PDI 10 first authenticates the security manager as the source of messages received from it using an on-board public key of the security manager. The cryptographic software module of the PDI is configured to sign a message digest generated and forwarded to the PDI by the security manager, based on a message from an external application. Before the PDI signs such a message digest, it authenticates that the message digest actually came from the security manager by verifying the security manager's key used to create the digest. This safeguards the PDI against being spoofed into signing any document other than one which it should be signing.

For the closed system of the present invention the cryptographic infrastructure is relatively simple and comprises a database record of the public keys supported by a single layer hierarchy and a secure server to providing on-line validation of digital signatures.

A biometric software component is included in the biometric acquisition component 35 of each PDI 10. This software component converts a digital representation of a biometric image received from the fingerprint microchip 35 to a template and tries to match that template to a master template of the user's biometric which has been captured and stored at the time the user is registered with the security system. A matching algorithm of the biometric component compares a template generated from an input real time (i.e. live) representation of the user's biometric (i.e. input from the fingerprint microchip) with the master template stored on the PDI in secure memory 25 and outputs, for transmission to the security manager, a digitally signed message containing the result of the comparison. At any given time, pursuant to a request by the policy manager component 320 or at predetermined time intervals, the PDI 10 is able to verify a user by comparing a new template derived from the user's input biometric, in real time, with the stored template and such verification is conducted wholly on-board the PDI 10 (i.e. using only its own facilities) without any dissemination of the stored data used to do so.

The PC 100 includes a device manager software component (DM) 150 which receives information from the BU 50 and, in turn, communicates with the transaction manager component (TM) 380 running on the central server(s) 300. When the BU 50 loses communications with the PDI 10 for an assigned predetermined time period the conversation between the BU 50 and PDI 10 is ended and the TM 380 notifies a policy manager component (PM) 320 that the PDI 10 is no longer within the predetermined detection envelope. When the TM 380 receives notice that a new PDI 10 has been detected by the BU 50 it instructs the PC 100 to display status information about the log-on process to the detected user and, if appropriate, invites an authorized user to log-on to the system. Depending upon the policy manager settings, any sensitive information currently displayed on the screen as part of an existing logged-in session is automatically blanked. The screen is not restored until the user of the newly detected PDI device has biometrically authenticated themselves with the security manager and the policy manager has determined that they have the right to view this data as an observer.

In addition, on being notified of a detected PDI the transaction manager component 380 directs the PC 100 to display (on its display screen) a visual identifier of the detected user, for example the name of the user or, preferably, the facial image of the user retrieved from the registration database. This provides two security checks. Firstly, a strong visible notification is thereby provided to an authorized user working with such display screen of the identity of all persons within viewing range of the screen and this assists the user to protect against unauthorized data access (in that the user then knows immediately the moment someone else comes with range to read the information displayed on the screen and can see exactly who that person is). Secondly, a user working at a screen would expect to see on the screen images of all person's that are in the area of the screen and if one such person's image is not detected the user would thereby be alerted that the PDI of the person not so detected is faulty and in need of charging, repair or replacement. Optionally, this feature may be used to control an entry point within a building to provide a workstation attendant (e.g. security guard) with an instant, automatic display of an image of the person who is registered to a PDI as a person/PDI pair pass by that workstation (the image so displayed and the person wearing that PDI should be the same in a secure situation). Similarly, if a malicious person attempts to view information to which they are not entitled access while another user is logged on, or if they attempt to gain entry to a secure location by wearing a disguise, the fact that their image is not displayed will immediately alert the legitimate users present that something is amiss.

The security manager component 340 manages the secure processes which take place between the PDI 10 and other components of the network security system such as the registration authority database 360 and also those messages sent by external applications to a user and vice versa which require verification and/or digital signatures. The security manager authenticates a PDI 10, using a challenge/response mechanism integrating digital signatures, whereby all further actions can be taken only by an authenticated user. The security manager also creates a message digest of any document(s) or transaction(s) to be transmitted to the user and a notarized log of all system events (the digital notarization process being well-known in the art and used to affix, to a signed document, both a time/date and a trusted third-party signature). In addition, the security manager may, depending upon the application, communicate and consult with a policy manager component 320 which applies business rules and workflow to provide granular control of data extracted from databases. This occurs in the situation where an application requires different levels of security for different users, that is, where different users are to have different levels of authorization for accessing data on the basis of a hierarchical classification such as where highly confidential data is to be permitted to a limited number of users only.

The security system utilizes a structured and rigorous process for registering a new user. An existing user to whom the system has assigned the privilege of registering new users (the registrar privilege), must be logged into the network and running a registration application which forms the front end of the registration authority component (RA) 360. A user (referred to herein as a guarantor) to whom the new user to be registered is known, may also be present at the same BU 50. The registration authority database contains information about users, their roles (e.g. guarantor) and their privileges of registering new users. In some circumstances, for instance, the user with registration privileges may also act in the role of guarantor. Some basic biographical data about a new user is then entered, possibly including the new user's name(s), address, date of birth, numbers of supporting documents used to establish identity, and any other specific data the system may have been configured to capture such as a facial image of the person. The data so entered is stored on the RA database only, and not on the PDI 10. The user is then handed a PDI device and the PDI's operability is tested by going through the steps of acquiring the PDI by a BU 50 of the PC 100 and checking the PDI using the security manager to ensure that it is in the correct state for assignment to a new user; if it is, then an enrollment process is started as follows.

Using its microprocessor(s) 20 the PDI device itself generates and internally stores the user's biometric template and one or more public and private keys. The PDI samples the new user's fingerprint until a consistent and satisfactory fingerprint template is achieved. The resulting achieved fingerprint template is not transferred to any external component of the system but is stored within the PDI device in its secure storage. No biometric information about the fingerprint ever leaves the PDI device. The PDI 10 is then instructed by the registration application to generate one or more key pairs and all private key(s) so generated always remain within the PDI 10 and are never transferred outside the PDI. The public keys so generated are forwarded to the central server 300 and stored in the RA database 360. The security manager also holds its own private keys in secure storage and the public key for at least one of these is provided to the PDI and held in the PDI's secure storage. These private and public keys are thereafter used by the PDI and SM to verify or create digital signatures, transactions and challenges directed to or from the new user's PDI. During the new user registration process the guarantor may be required to confirm their identity via the fingerprint chip on the guarantor's PDI device, so as to create a digital signature proving that the guarantor has vouched for the new user.

The PDIs 10 of the present security system are protected against tampering between the factory (the location of their manufacture) and the usage site (against events occurring either during initial delivery or for device maintenance) by cryptographic processes. Newly manufactured PDI devices are programmed with a public key of the security manager at the receiving institution and with an initial issuance private key. When these PDI devices are sent to the institution a list of their unique ID numbers are separately and securely communicated to the institution. During the process of registering a new user, the PDI authenticates itself to the security manager using the initial issuance private key (of which the security manager has the public key), and the security manager authenticates itself to the PDI using its private key. Additionally, the PDI device's unique ID number is communicated to the security manager and this is matched against the list of PDI device ID numbers received from the factory. This protocol protects against the construction of fraudulent devices and the same protocol is used for PDI devices returned to the institution following maintenance at the factory.

Log-on and other privileges are available on a given network domain only to PDIs which have registered with the registration authority associated with that network domain, but because each PDI 10 also has a unique ID number it is recognized by the security manager regardless of the particular registration authority which was used originally for its registration. Therefore, the global nature of the ID number of the PDI permits an integration of different security systems (i.e. systems operating under different registration authorities) by sharing the databases of the different registration authorities.

Figure 4A:
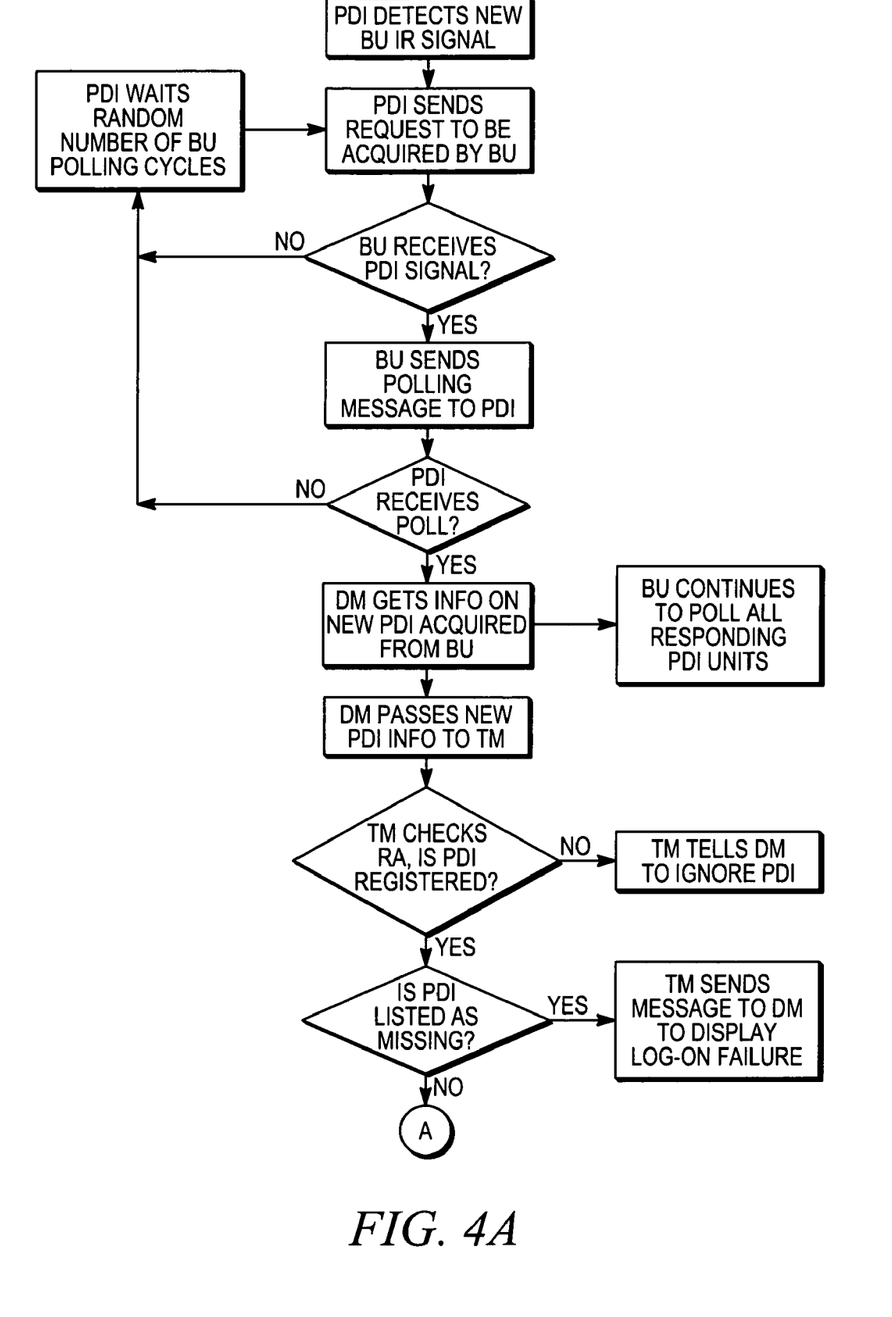
FIGS. 4(a), 4(b) and 4(c) are flow chart diagrams illustrating a user acquisition and log-on process in accordance with the present invention; and, FIGS. 5(a) and 5(b) are flow chart diagrams illustrating the process used by the security system of the preferred embodiment of the invention for producing digital signatures.
Figure 4B:
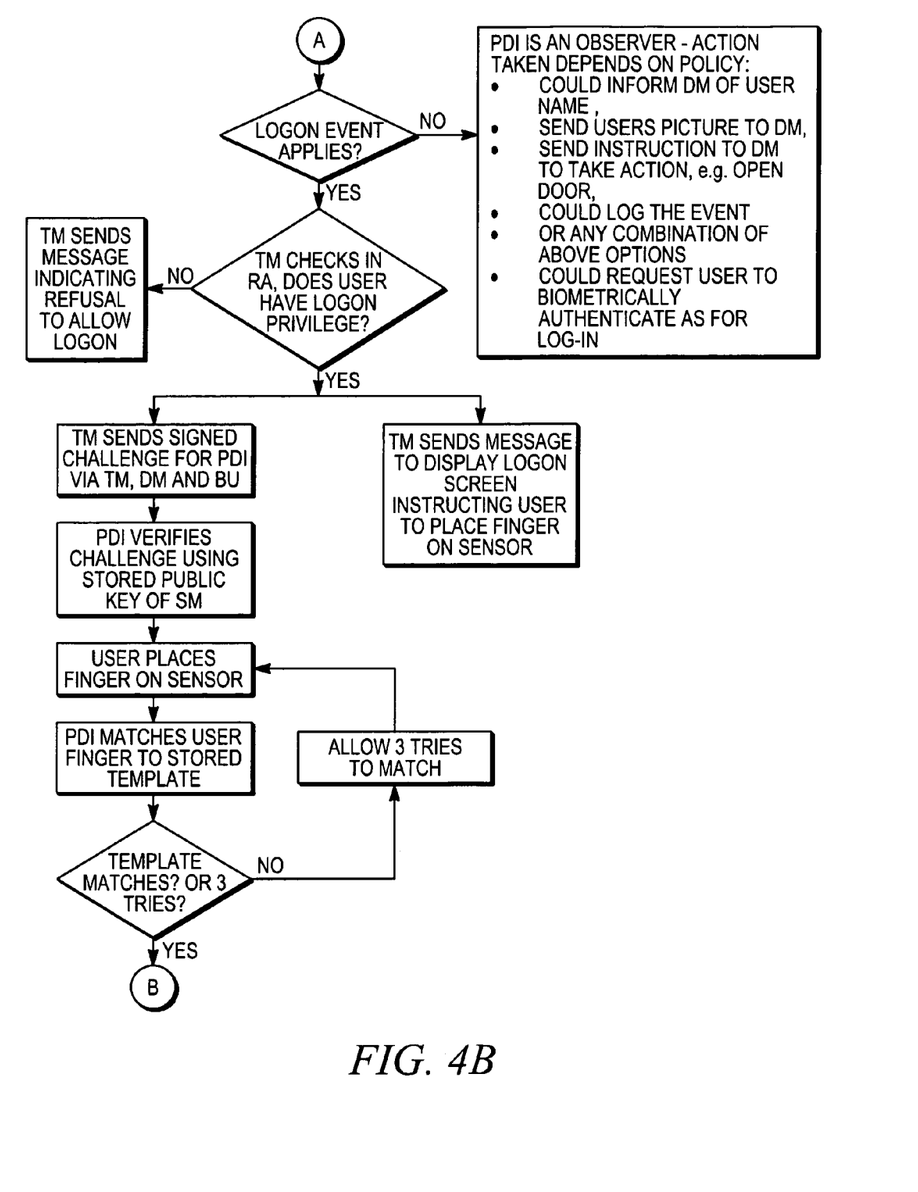
Figure 4C:
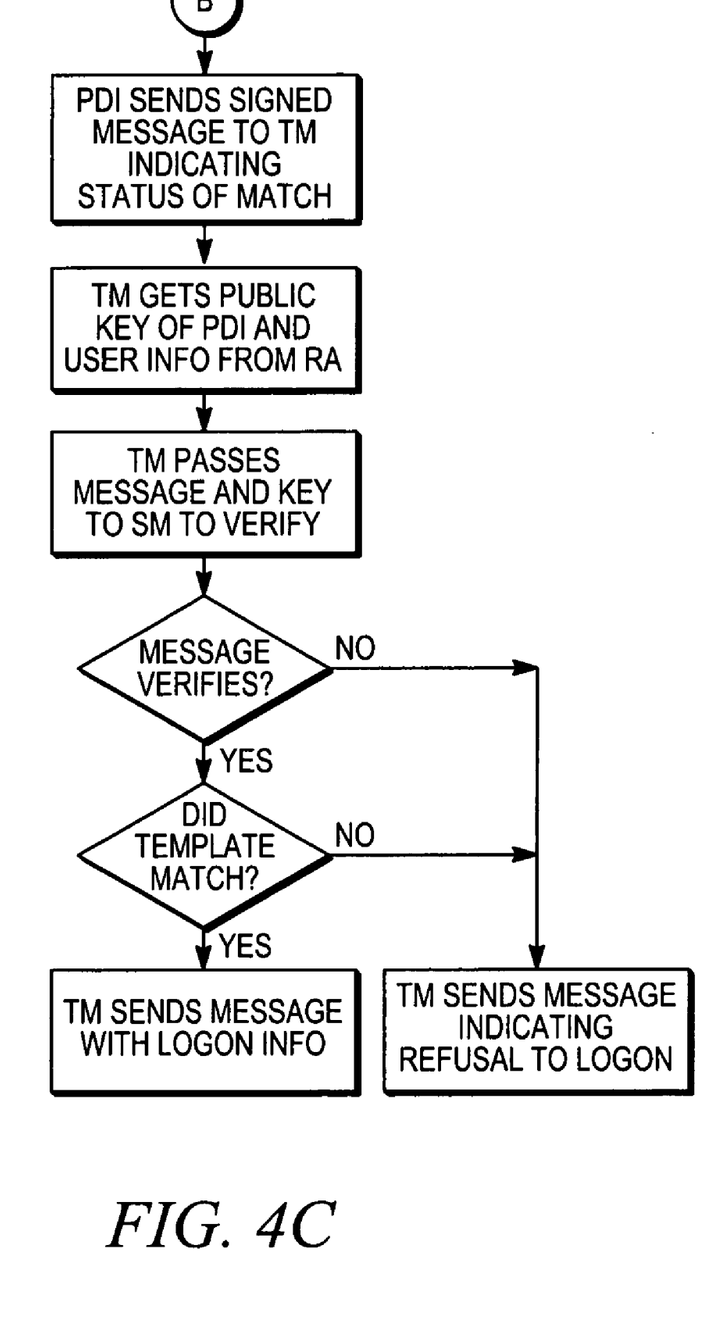

The steps performed by the security system during the acquisition (i.e. the detection by a BU 50 that a PDI 10 is in range) and subsequent verification of a PDI for log-on access are described by the flowchart of FIGS. 4(*a*) though 4(*c*). The BU transmits a constant IR signal to all points surrounding the PC 100/BU 50 which are within the detection envelope. As soon as a PDI enters into that envelope it receives this IR signal of the BU and immediately responds to the BU initiating its acquisition by the BU. The BU then adds the PDI to the polling loop. A PDI is acquired by any BU for which it is in range regardless of whether the PDI is registered on the system or not. The acquisition step is conducted at a low process level whereby the BU adds the new PDI device to a polling loop for monitoring the PDI and sends a message to the central security manager identifying and querying the unique ID number of the PDI. If the PDI is a registered device on the system, the user has a log-on privilege and there is no one logged on the PC 100 (workstation), the user will be invited to log onto the PC 100. If the PDI is a registered device on the system but someone is already logged onto the PC 100, any sensitive information (as determined by the policy manager) may be immediately blanked, and a visual identifier of the user associated with the detected PDI be displayed on the PC 100. Depending on the privileges of this new user to view the data associated with the currently logged-in session, the new user may then be permitted to biometrically authenticate himself/herself and remain as an observer. This occurs through the same process as the rest of the normal log-on, except that in the last step the TM will record the presence of the observer and request the network application or the PC 100 to restore the screen, rather than to log on the user. For a user either attempting to log on or to become an observer, the next step is that the SM prepares a challenge message which has some randomly chosen information in it and which the SM digitally signs with its private key. This message is then transferred to the PDI device. The user is invited by a screen display to log-on (optionally including their name) by placing their finger on the fingerprint chip and confirming their identity. The PDI device first confirms that it has received a message from the legitimate SM process by verifying the digital signature on the message using the public key of the SM which is stored on the PDI device. The user's fingerprint is then acquired and the template extracted and compared to the template stored on the device. If there is a match then a message is sent back to the SM which contains the challenge and confirms that the user has been biometrically authenticated. This message is digitally signed by the PDI device using its private key stored on board. The confirming message is authenticated by the SM using the public key of the PDI device which is stored in the registration authority and checked to ensure that the challenge has been correctly returned. This safeguards against any replay attack. If the PDI device is being used as the authentication means for a single sign-on (SSO) process, in which log-on access is granted to a PC 100 on a network, the TM 380 then sends a message to the log-on component on the PC 100 requesting that the user be logged on.

If the PC 100 user is already logged onto the PC 100 and desires access to a specific network based application or applications, then the TM 380 will mutually authenticate itself, through the SM, with a secure server running the application(s) and will inform this server that the user has been logged in. In the healthcare area, for instance, there is an emerging standard for context management on PCs called CCOW (Clinical Context Object Workgroup) which allows sharing of log-ons. The TM 380 would then interact with the CCOW-enabled applications to allow the user access only to that subset of applications and data which have been determined to be appropriate by the policy manager 320, using the information about the user's roles and privileges obtained from the registration authority 360 database. In general, the security manager 340 and policy manager 320 together act as a security filter on all network applications and data, throughout the user's logged-in session.

A PDI may be recorded in the security system as being missing or stolen. In this situation, once the PDI is acquired the SM verifies the PDI and, as a result of this, determines that the PDI is listed as missing. The BU which acquired the PDI is known by the security manager and, in addition, the security manager knows both the location of that BU and the proximity of the PDI to that BU. This information identifying the location of the PDI is then communicated to a designated user (such as an administrator or security coordinator) in order that the missing PDI may be retrieved and if it has been stolen the responsible party can be apprehended.

During the user's logged-in session, following the log-on, the PDI device and the base unit communicate periodically to ensure that the PDI is still within the detection envelope and this conversation includes cryptographic communications which ensure the base unit is able to detect any attempt by another (unauthorized) device to insert messages into the communication stream. If the user's PDI stops communicating with the BU for a first predetermined time period, for example if the user walks away from the workstation in order to get something, the DM directs the workstation to carry out a predetermined log off process to ensure that no unauthorized person can continue using the application in place of the authorized user. This may be a temporary automatic log off by which the DM will direct a resumption of the operation of the application at the point the user was at when the BU lost its ability to communicate with the user's PDI if the user's PDI is detected again within a short second predetermined time period. Optionally, the system may be configured to require the user to biometrically reverify their presence with the PDI during the logged-in session, and this may be triggered randomly, by elapsed time, or by policy manager 320 decisions based on the user's access to specific data or applications. This ensures that the user remains physically present with the PDI during the entire logged-in session.

In the acquisition/verification process, as described by the flowchart of FIGS. 4(*a*) through 4(*c*), the system establishes a tight link, in both space and time, between the biometric authentication of the user and the cryptographic verification of the PDI, user and security manager so as to securely establish that the authorized user is present with the PDI assigned to that user and is communicating correctly with the security manager. The identity of the user is verified in real time, on-board the PDI as described herein by comparing the stored biometric template with the biometric template generated from the live biometric transducer (e.g. fingerprint microchip), both of which are retained within the PDI throughout this process. The PDI and security manager each verify each other by using digital signatures communicated according to a challenge/response protocol and the security manager is notified by the PDI in real time, for any given document/transaction signature, of the identity of a user by means of a digitally signed message.

Figure 5A:
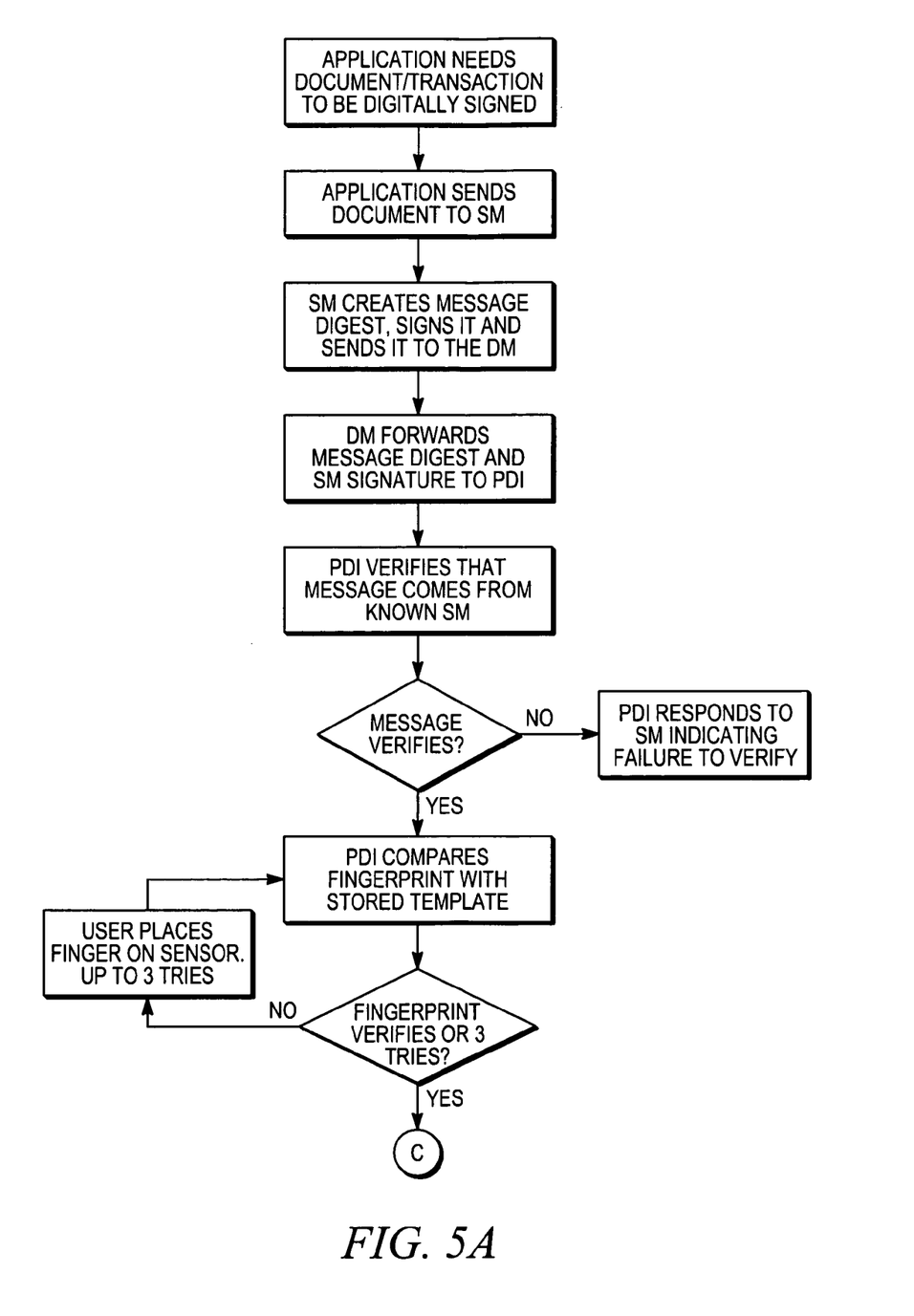
Figure 5B:
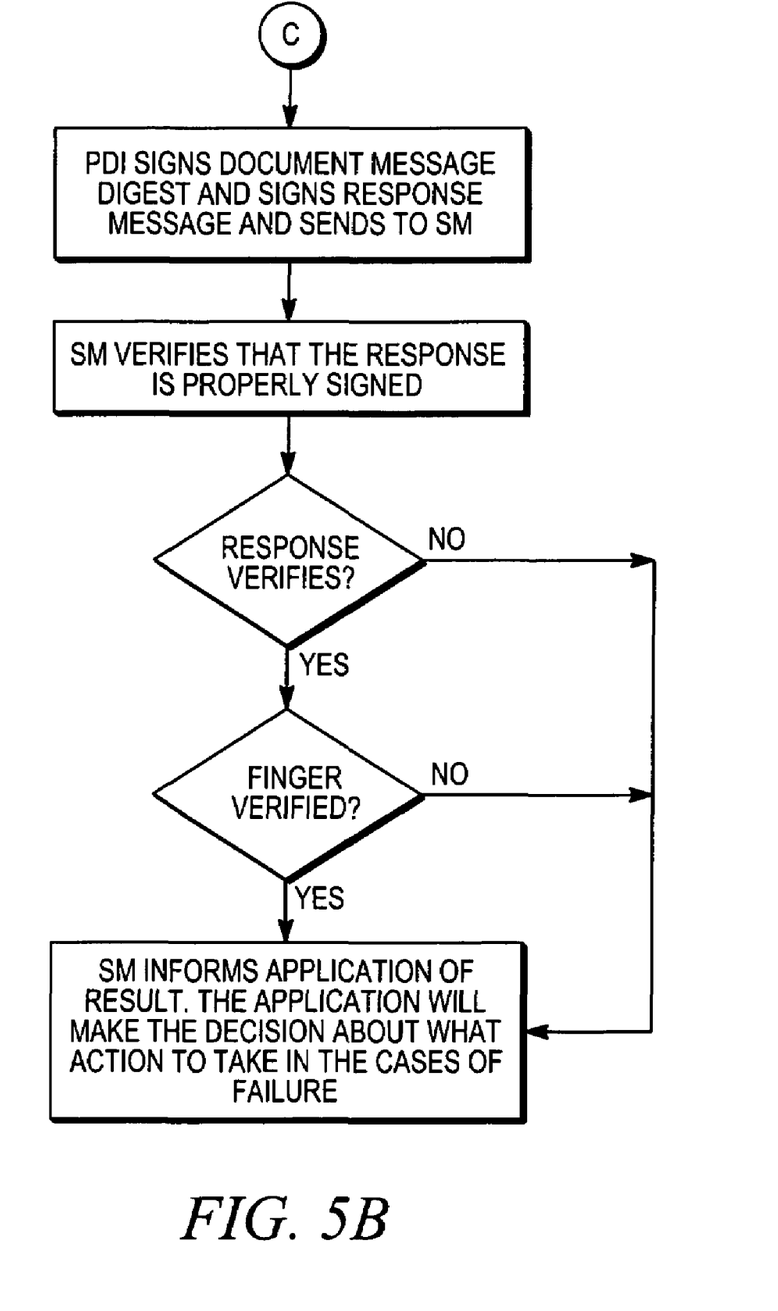

In the course of using an application there may be a requirement for the user to digitally sign a document or other form of transaction (e.g. a drug prescription). The steps taken by the system to create a digital signature for a document/transaction are described by the flowchart of FIGS. 5(*a*) and 5(*b*). The signing process is requested by the application, which forwards the document/transaction to be signed to the SM. The SM creates a message containing the source and destination addresses, a message digest of the document/transaction, a time stamp and random data. This message is then digitally signed and forwarded to the PDI device.

The PDI device first verifies the signature of the SM and this prevents the possibility that another process might make a signing request of the PDI device or that the message digest could be tampered with or substituted. If the signing request includes a requirement for confirming the user's identity then it is the responsibility of the application to request the user to actively digitally sign the document or transaction currently under review. The user should then place their finger on the fingerprint chip. The PDI device then waits for the user to place their finger on the device. Once a finger placement is detected, the image is captured, processed, and compared to the stored template. If the template matches the presented finger, a message is created containing the source and destination addresses, the message digest of the original document transaction and random data. This message is then digitally signed and sent to the BU where it is forwarded to the SM. If the finger does not match the template, the user is permitted a certain number of retries, after which, a digitally signed message indicating the failure to match is sent to the SM. The SM looks up the public key of the PDI device using the PDI device's unique ID and the message is verified using this information. At this point, the result of the identity authentication is passed to the application requesting the authentication and, if necessary, a copy of the digitally signed message is sent to a secure notarization service.

The digital signature can be used to ensure that the data of the basic document/transaction has not been changed after the fact. Given the nature of the foregoing process, including the biometric verification of identity, it can also function to rebut any attempt by the user to repudiate the signature.

The present security system provides real-time positive authentication of a user's presence at a particular network access point and it sets up and monitors a secure encrypted path between the network access point and a chosen network server. It further provides a reliable means for collecting digital signatures.

The individual electronic and processing functions utilised in the foregoing described preferred embodiment are, individually, well understood by those skilled in the art. It is to be understood by the reader that a variety of other implementations may be devised by skilled persons for substitution. Persons skilled in the fields of electronic security systems and communications design will be readily able to apply the present invention to an appropriate implementation method for a given application.

Consequently, it is to be understood that the particular embodiment shown and described herein by way of illustration is not intended to limit the scope of the invention claimed by the inventors which is defined by the appended claims.

What is claimed is:

1. A personal digital identifier device for controlling access to a computer network, said network comprising a plurality of workstations each having a base unit associated therewith, said base unit being configured for wireless communications with said personal digital identifier device, and said network further comprising a central server utilizing a security manager component and network storage, said security manager component associated with a private key and a corresponding public key and said network storage containing a public key corresponding to a private key held by said personal digital identifier device, said personal digital identifier device being lightweight, configured for wearing and/or carrying by a user registered thereto and comprising:

(a) a wireless communications component comprising a transceiver for communicating with said base unit;

(b) a biometric acquisition component for obtaining a user's input biometric and producing a digital representation thereof;

(c) a processor configured for communicating with said transceiver and said biometric component and operable for:

(i) evaluating whether a template derived from said digital representation corresponds to a master template derived from a user's biometric digital representation previously produced by said biometric component and generating a matching signal when such a correspondence is determined;

(ii) generating said private key held by said personal digital identifier device and said public key corresponding thereto and outputting said generated public key for transmission by said transceiver;

(iii) producing a digital signature using said private key; and, (iv) verifying, using said public key for said private key associated with said security manager component, that the source of an encrypted message ostensibly received from said security manager is said security manager component;

(d) secure storage containing said master template of a user's biometric, said generated private key and said public key for said private key associated with said security manager component;

(e) a power source; and, (f) a housing, said personal digital identifier device being configured for producing, using said generated private key, a digitally signed challenge response message following said generating of said matching signal in response to a challenge message received from said security manager component and for transmitting said response message, and said personal digital identifier device being configured to prevent transmission of any of said master template of a user's biometric and said private key, and wherein, during a currently logged-in session of the user associated with the personal digital identifier device, a policy manager component directs at least one of the workstations to blank out a respective screen when a second personal digital identifier device is detected at a location within an envelope until such time as a user registered to said second personal digital identifier device is biometrically identified to have permission to view data of the currently logged-in session.

2. A personal digital identifier device according to claim 1 wherein said biometric component includes a transducer.

3. A personal digital identifier device according to claim 2 wherein said transducer comprises a solid state fingerprint sensor.

4. A personal digital identifier device according to claim 3 wherein said transceiver transmits and receives optical signals.

5. A personal digital identifier device according to claim 4 wherein said transceiver transmits and receives radio frequency signals.

6. A personal digital identifier device according to claim 1 wherein a response signal is automatically transmitted from said transceiver in response to a signal received by said transceiver from one said base unit.

7. A personal digital identifier device according to claim 1 wherein all data held in said secure storage is by itself non-identifiable of said user.

8. A personal digital identifier device according to claim 1 in combination with a device holder wherein said device holder is configured to co-operate with said housing of said personal digital identifier device such that said personal digital identifier device is held by said holder device when it is appropriately positioned relative to said holder device, said device holder comprising a communications connector for communicatively coupling said personal digital identifier device directly to one said workstation when said personal digital identifier device is held by said device holder.

9. A security system for controlling access to a computer network at a network access point comprising a workstation, said system comprising:

A. a personal digital identifier device comprising:

(a) a wireless communications component comprising a transceiver;

(b) a biometric acquisition component for obtaining a user's input biometric and producing a digital representation thereof;

(c) a processor configured for communicating with said transceiver and said biometric component and operable for:

(i) evaluating whether a template derived from said digital representation corresponds to a master template derived from a user's biometric digital representation previously produced by said biometric component and generating a matching signal when such a correspondence is determined;

(ii) generating a private key to be held by said personal digital identifier device and a public key corresponding thereto and outputting said generated public key for transmission by said transceiver;

(iii) producing a digital signature using said private key; and, (iv) verifying that an encrypted received message is from a security manager component using a public key for a private key associated with said security manager component; and, (d) secure storage containing said master template of a user's biometric, said generated private key and said public key for said private key associated with said security manager component, said personal digital identifier device being configured for producing, using said generated private key, a digitally signed challenge response message following said generating of said matching signal in response to a challenge received from said security manager component and for transmitting said response message, and said personal digital identifier device being configured to prevent transmission of any of said master template of a user's biometric and said private key;

B. a base unit associated with said workstation and configured for initiating and maintaining wireless communications with said personal digital identifier device, said communications extending over an area defined by an envelope associated with said workstation, wherein, during a currently logged-in session of the user associated with the personal digital identifier device, a policy manager component directs the workstation to blank out the screen when a second personal digital identifier device is detected at a location within said envelope until such time as a user registered to said second personal digital identifier device is biometrically identified; and, C. a central server having access to network storage and utilizing said security manager component and said personal digital identifier device for authenticating said user, said network storage containing a public key corresponding to said private key generated by said personal digital identifier device.

10. A security system according to claim 9 wherein said biometric component includes a transducer.

11. A security system according to claim 9 wherein said workstation is a personal computer.

12. A security system according to claim 9 wherein said base unit regularly transmits a first signal to said personal digital identifier device and said personal digital identifier device automatically transmits a response signal in response thereto when said personal digital identifier device is within said envelope.

13. A security system according to claim 12 comprising a plurality of said personal digital identifier devices, a plurality of workstations and a plurality of base units wherein a base unit is associated with each said workstation, each said base unit transmitting a polling signal to each said personal digital identifier device within said base unit's associated envelope following said base unit's receipt of said response signal from each said personal digital identifier device.

14. A security system according to claim 9 wherein all data held in said secure storage of said personal digital identifier device is by itself non-identifiable of said user.

15. A security system according to claim 9 wherein said network storage includes data identifiable of said user for display on a screen of said workstation when said user's personal identification device is located within said envelope.

16. A security system according to claim 9 wherein said envelop has a shape and area which are configured to encompass those locations proximate to said workstation at which an observer may read and/or understand information displayed on a screen of said workstation.

17. A method for controlling access to a computer network in which workstations provide points of access to said network, said network including a central server communicating with said workstations and secure network storage, and a base unit configured for initiating and maintaining wireless communications with a portable personal digital identifier device carried or held by a user being associated with each said workstation, said wireless communications extending over an area defined by an envelope associated with said workstation, said method comprising the steps:

(a) on registration of a first portable personal digital identifier device to a first user, within said first portable personal digital identifier device: receiving an input biometric of said user, producing a digital representation thereof, deriving from said digital representation a master template, securely maintaining said master template in storage, generating and securely maintaining in said storage a private key, generating a public key corresponding to said generated private key and providing said generated public key for storage in said network storage and receiving and storing in said storage a public key for a private key associated with a network security manager component;

(b) transmitting a first signal from a base unit associated with one said workstation to said first personal digital identifier device and automatically transmitting from said first personal digital identifier device a response signal establishing communications between said base unit and said first personal digital identifier device in response to said first signal when said first personal digital identifier device is within said envelope;

(c) receiving at said first personal digital identifier device a digitally signed challenge message ostensibly from said network security manager component and verifying within said first personal digital identifier device the origin of said challenge using said public key for said private key associated with said security manager component;

(d) acquiring on said first portable personal digital identifier device an input biometric of said user, producing a digital representation thereof and deriving from said digital representation a biometric template;

(e) evaluating within said first portable personal digital identifier device whether said biometric template corresponds to said master template and generating a matching signal when such a correspondence is determined;

(f) producing within said first personal digital identifier device, using said generated private key, a digitally signed challenge response message following said generating of said matching signal in response to said challenge message and transmitting said response message to said security manager component to authenticate said first user;

(g) permitting said authenticated first user to access said computer network through said workstation; and (h) during a currently logged-in session of the first user associated the first personal digital identifier device, directing the workstation to blank out the screen by a policy manager component when a second personal digital identifier device is detected at a location within said envelope until such time as a second user registered to said second personal digital identifier device is biometrically identified to have permission to view data of the currently logged-in session.

18. A method according to claim 17 and further comprising configuring the shape and area of said envelope to encompass those locations proximate to said workstation at which an observer may read and/or understand information displayed on a screen of said workstation.

19. A method according to claim 17 and further comprising, following said base unit's receipt of said response signal from said personal digital identifier device, transmitting from said base unit a polling signal to said personal digital identifier device for determining whether said personal digital identifier device remains located within said base unit's associated envelope.

20. A method according to claim 17 and further comprising displaying on a screen of said workstation data identifying said user when said user is identified.

21. A method according to claim 17 and further comprising initially registering said user by a registrar in the presence of a guarantor, said registrar and guarantor each being a registered user of the computer network and said registrar having access to the computer network and verified by said security manager component to have registration privileges, and requiring: that said guarantor provide to said security manager component a biometrically digitally signed message to authenticate said guarantor and that each of said registrar, guarantor and user remain within said envelope during said registering of said user.

* * * * *

UNITED STATES PATENT AND TRADEMARK OFFICE
CERTIFICATE OF CORRECTION

PATENT NO. : 7,310,734 B2  Page 1 of 1
APPLICATION NO. : 09/775205
DATED : December 18, 2007
INVENTOR(S) : Alan Boate It is certified that error appears in the above-identified patent and that said Letters Patent is hereby corrected as shown below:

Title Page,
Item (57), ABSTRACT, Col. 2, Line 2, after "network", insert in place thereof
-- access --.

Item (56), REFERENCES CITED, OTHER PUBLICATIONS, Page 2, Col. 2, Lines 1-2, delete "netwworks" and insert in place thereof -- networks --.

Item (56), REFERENCES CITED, OTHER PUBLICATIONS, Page 2, Col. 2, Line 11, delete "Krishnan" and insert in place thereof -- Krishan --.

Column 12,
Line 13, delete "document transaction" and insert in place thereof
-- document/transaction --.

Line 64, delete "andlor" and insert in place thereof -- and/or --.

Signed and Sealed this

Eighth Day of July, 2008

JON W. DUDAS
*Director of the United States Patent and Trademark Office*